United States Patent [19]

Bajaj

[11] Patent Number: 5,053,008
[45] Date of Patent: Oct. 1, 1991

[54] INTRACARDIAC CATHETER

[76] Inventor: Sandeep Bajaj, 512 Grinell Dr., Richmond, Va. 23236

[21] Appl. No.: 616,899

[22] Filed: Nov. 21, 1990

[51] Int. Cl.⁵ ............................................... A61H 1/00
[52] U.S. Cl. .................................... 604/104; 606/200; 128/24 AA
[58] Field of Search ............. 129/899, 24 AA, 662.06, 129/660.03; 606/200, 1; 604/104

[56] References Cited

U.S. PATENT DOCUMENTS

| | | | |
|---|---|---|---|
| 4,706,671 | 11/1987 | Weinrib | 604/104 |
| 4,870,953 | 10/1989 | DonMicheal et al. | 128/24 AA |
| 4,873,978 | 10/1989 | Ginsburg | 606/200 |
| 4,957,501 | 9/1990 | Lahille et al. | 604/104 |
| 4,969,891 | 11/1990 | Gewertz | 128/899 |

Primary Examiner—Francis Jaworski
Assistant Examiner—George Manuel
Attorney, Agent, or Firm—Whitham & Marhoefer

[57] ABSTRACT

A multisheathed catheter (12) includes an umbrella (18) positioned on its exterior sheath (16). In use, the umbrella (18) should be positioned within the pulmonary artery. The umbrella (18) has a meshwork (22) through which blood and plasma pass freely therethrough, but which is capable of catching emboli and other foriegn matter before they travel to the lungs. Detection equipment, including a two-dimensional ultrasound probe (44), differential sensors (54 and 56), and chemical sensors (44), are positioned to detect when an embolus has been caught in the umbrella (18). A conduit (64) transports lysing agents (66) such as TPA or heparin to the trapped embolus. In addition, the umbrella (18) can be closed on a trapped embolus using cords (34) and the embolus can be broken apart using ultrasonic probes (70) or can be removed by suction after it is drawn inside the lumen of the catheter (12).

33 Claims, 4 Drawing Sheets

INTRACARDIAC CATHETER

BACKGROUND OF THE INVENTION

1. Field of the Invention

The present invention generally relates to catheters used during surgery and, more particularly, to an umbrella style catheter which is temporarily placed in the main pulmonary trunk of a patient to detect, prevent and treat pulmonary emboli.

2. Description of the Prior Art

Pulmonary embolism is one of the most misdiagnosed of the serious acute disorders encountered by clinicians and is estimated to be the third most common cause of death in the United States. As many as 200,000 people die each year as a result of pulmonary embolism. Approximately 650,000 patients in the United States are affected by symptomatic pulmonary embolism each year. As many as sixty percent of the patients who develop pulmonary embolism are not diagnosed as having the condition until after their death. If no specific treatment is initiated following pulmonary embolism, the incidence of fatal recurrent embolism is approximately thirty percent.

Thrombi or blood clots can form in a patient's veins, particularly large veins, under certain conditions and these blood clots can dislodge from the veins and travel to the lungs where they can occlude the pulmonary vessels. The impact that thrombi which have dislodged and travelled to a patient's lungs can have on the patient can vary from sudden death to no perceptible change in well being. The following have been described as the primary sites of thrombus formation: (1) the iliac vein (especially the external iliac vein), (2) the common femoral or proximal thigh vein, (3) the termination of the deep femoral vein, (4) the popliteal vein, (5) the posterior tibial vein, and (6) the calf veins. Thrombi in the calf veins are the most common, but are the least likely to embolize. Thrombi in the proximal thigh and iliac veins are most likely to embolize.

The formation of a clot in the veins involves either injury to the vessel wall and/or associated slowing of blood flow. The production of a permanent hemostatic plug results from the combined activities of endothelial cells, platelets, red cell, and coagulation cascade. When venous thrombi dislodge from their site of formation, they flow with the blood through the venous system to the pulmonary circulation. If the thrombus is extremely large, it can stop at the bifurcation of the pulmonary artery and form a "saddle embolus" which is instantly fatal. The majority of emboli dislodge to distal parts of the lung.

Emboli in lobar and segmental pulmonary arteries are associated with humoral vasoconstriction and bronchoconstriction which are known to potentiate vascular injury in patients without prior cardiopulmonary disease. Right ventricular afterload increases when the pulmonary artery obstruction reduces the vascular bed by greater than twenty five percent. To compensate for such an impairment, the right ventricular and pulmonary artery pressures rise. A normal right ventricle can generate a maximum pulmonary artery systolic pressure of approximately 40 mm Hg at standard temperature and pressure. As the right ventricular outflow pressure rises acutely, the right ventricle dilates and becomes hypokinetic and fails, resulting in cardiogenic shock. When cardiac function has been compromised by previous cardiopulmonary illness, relatively smaller emboli obstructing only one or two segments can exert a similar hemodynamic effect. Because of the anatomical juxtaposition of the two ventricles, right ventricular dilation adversely affects the left ventricular filling function and can cause left ventricle failure as well.

Pulmonary embolisms have been classified into three broad categories: Massive Pulmonary Embolism, Submassive Pulmonary Embolism, and Smaller Pulmonary Embolism. Massive pulmonary embolism results from a twenty five percent or greater obstruction of the pulmonary vascular bed. The most common symptoms of massive pulmonary embolism are fainting, corpulmonale, and cardiogenic shock or cardiac arrest. Submassive pulmonary embolism can be defined as an embolism to one or more pulmonary segments not accompanied by elevation in right ventricular and pulmonary artery systolic pressures. The most frequent symptoms of submassive pulmonary embolism are dyspnea and pleuritic chest pain. Although the patients do not succumb to an acute episode, unlysed thrombus in the pulmonary artery could eventually lead to chronic pulmonary hypertension; a syndrome of progressive right heart failure and corpulmonale (this condition develops when pulmonary embolism is either not diagnosed or is treated inadequately). Smaller pulmonary embolisms can result with occlusions of small peripheral pulmonary arteries. Bronchoconstriction can result from smaller pulmonary embolisms and collateral flow via bronchial vessels may not be preserved which could lead to pulmonary infarction. The clinical diagnosis of a pulmonary embolism is routinely confirmed by either a lung scan or pulmonary angiography. Typically, symptoms and signs develop three to seven days after the onset of an embolism. Treatment of the embolism is usually by anticoagulation for one to three weeks together with use of analgesics and supportive care.

Clinical suspicion is an important step toward diagnosis of a pulmonary embolism. Over-diagnosis or under-diagnosis can occur because signs and symptoms often are not maintained long enough to discriminate between patients with true pulmonary embolism and those without pulmonary embolism. The most common symptoms are shortness of breath, pleuritic chest pain, apprehension, and coughing. The most common signs are tachypnea (fast breathing) with a respiration rate (RR>16/min), Rales, accentuated second heart sound, and tachycardia.

Perfusion lung scanning is an important diagnostic test in screening for pulmonary embolism. A normal lung scan essentially rules out most pulmonary embolisms and directs clinical attention to other diagnostic possibilities. Abnormal lung scans are categorized as being (1) low probability of pulmonary embolism, (2) moderate probability of pulmonary embolism, and (3) high probability of pulmonary embolism. As a general practice, patient's with a high probability of pulmonary embolism are treated with intravenous heparin (a blood thinner), patient's with a low probability of pulmonary embolism are not treated, and patient's with a moderate probability of a pulmonary embolism are either further evaluated with pulmonary angiography or are treated with intravenous heparin if angiography is not available and clinical suspicion is high. Pulmonary angiography has been considered the definitive test for the diagnosis of pulmonary embolism; however, the equipment needed is typically only available at large tertiary hospitals and university centers and is under-used even where it is available. The largest prospective study comparing abnormal lung scan and pulmonary angiography, performed by Hull et al. at Duke University, had the following results: 66% of the patient's with high probability of pulmonary embolism lung scans had a positive angiogram, 32% of patient's with moderate probability of pulmonary embolism lung scans had a positive angiogram, and 15% of the patient's with low probability of pulmonary embolism lung scans had a positive angiogram (note, as discussed above, these people would not ordinarily be treated). Moreover, 39% of the patient's with indeterminate lung scans had positive angiograms. Hence, the Hull et al. data underlines the importance of making pulmonary angiography more widely available.

Other modalities that are helpful in pulmonary embolism diagnosis are doppler echocardiogram computed tomography, digital substraction angiogram, magnetic resonance imaging, indium labeled platelet imaging, fiberoptic angioscopy. The presence of arterial blood gases, analysis of pleural fluid, electrocardiogram, blood tests, and chest X-rays can also indicate the presence pulmonary embolism. Tests used to diagnose deep venous thrombosis in the legs and pelvis include impedance plethysmography, B-mode ultrasonography and venography.

Patient's with certain risk factors are strongly predisposed to deep venous thrombosis and pulmonary embolism. Hypercoagulable states are the primary risk factors and they include antithrombin III deficiency, protein C and protein S deficiency, lupus anticoagulant, and deficiencies of minor blood factors. Secondary risk factors include abnormalities of coagulation and fibrinolysis such as malignancy, pregnancy, use of oral contraceptives, infusion of prothrombin concentrates, and nephrotic syndrome, abnormalities of platelets associated with myeloproliferative, diabetes mellitus, and heparin induced thrombocytopenia, and abnormalities of blood vessels and rheology. Conditions which promote venous stasis include immobilization, obesity, advanced age, and post operative state. Other conditions resulting in secondary hypercoagulable states include artificial surfaces such as grafts, vasculitis and chronic occlusive arterial disease, homocystinuria, hyperviscosity associated with polycythemia, leukemia, sickle cell disease, leukolutination, and increased serum viscosity.

Patient's with certain clinical conditions are predisposed to pulmonary embolism. For example, patient's who have had hip surgery, stroke or cerebral hemorrhage, major trauma, major abdominal or pelvic surgery, neurosurgery, neoplasm, sepsis, or cardiorespiratory failure all are at risk of developing pulmonary embolism. In addition, patient's that are immobilized, obese, over age 65, or have chronic medical conditions (cardiac, respiratory, or gastrointestinal) are predisposed to developing pulmonary embolism. Malignant cells, air, fat, bone marrow, amniotic fluid, tissue sites of injury, parasites and foreign materials are still other sources of pulmonary embolism.

As these risks and conditions have been identified, strong focus has been put on the prevention of deep venous thrombosis in high risk subgroups. Preventive treatment has resulted in a decreased incidence of pulmonary embolism in the last decade, but the decline has not been of a sufficient magnitude to attain acceptable levels. Conventional medical support in patients with pulmonary embolisms includes analgesia, oxygen, positive airway pressure, intubation for oxygenation or ventilation (which are unsatisfactory when unassisted), hyperventilation, positive end-expiratory pressure, and volume expansion. Blood thinners such as heparin have been used to treat pulmonary embolism for the past two decades. Heparin does not lyse the clot, but prevents clot enhancement and propagation and allows the patient's fibrinolytic system to stabilize and dissolve the clot over a period of time.

Unfortunately, based on most angiographic series, 30% to 60% pulmonary emboli are anatomically massive. As hemodynamic profile is more important, and underlying cardiopulmonary disease and humoral responses have significant influence, in autopsy series among all patient's dying from fatal pulmonary emboli, whether death occurs suddenly or more slowly, only half of the pulmonary embolisms meet the anatomical definition of massive.

In 1973 and 1974, urokinase and streptokinase, which are agents that cause clotting lysis, were investigated by the National Heart, Lung, and Blood Institute in the UPSET trial. Mortality from massive pulmonary embolisms was 33%; and whether heparin, urokinase, heparin or vena caval interruption, or heparin-streptokinase-embolectomy were used to treat massive pulmonary embolisms without shock, the mortality ranged from 5% to 7.7%. Also, apart from the transient immediate improvement in hemodynamics, the long-term survival between patients treated with thrombolysis and other aggressive measures or with traditional heparin therapy was the same. Moreover, patients treated with streptokinase and urokinase had more bleeding complications. It is estimated that only 10% of the patients with massive pulmonary embolisms survive long enough for angiographic analysis. However, the patients who do survive long enough to be diagnosed have benefitted from thrombolytic therapy, and in 1977 the Food and Drug Administration (FDA) approved the use of thrombolytic agents for pulmonary embolism.

More recently, tissue plasminogen activator (TPA), a selective thrombolytic agent which has been used nationwide for acute coronary thrombolysis, has been used to treat pulmonary embolisms. Dr. Goldhaber, at Harvard University, analyzed thirty six patients who were treated with TPA. It was noted that TPA treatment led to hemodynamic and angiographic improvement; however, only unilateral pulmonary angiograms were studied and only healthier patients were studied in that patients in shock (defined has having a systolic pressure less than 80 mm Hg) were not included in the investigation. In a recent report (1988) from a multicenter trial by Verstraete in Europe, TPA was given to 34 patients. Unfortunately, only four patients received thrombolysis within six hours of diagnosis, which is the most effective time for treatment. Nevertheless, the majority of patients were treated with TPA within 12-72 hours and a substantial number of them showed hemodynamic and angiographic improvement.

The chief surgical treatment for pulmonary embolism is embolectomy, i.e., surgical removal of the emboli. Even though this surgery was first performed in 1908, only after cardiopulmonary bypass was developed did it become standard therapy. Because of the critical state of the patients, embolectomy has a mortality rate of 25% to 50%. In a small group of patients, Dr. Greenfield and co-workers employed transvenous suction techniques for removal of emboli. In the transvenous suction experiments performed by Dr. Greenfield, embolic material was successfully removed from 13 of the fifteen patients (87%); however, four of the fifteen patients died.

Preventive surgical measures include ligation, plication or external clipping of the inferior vena cave, so that emboli can be prevented from propagating upstream. Inferior vena cava filters, which are permanent filters surgically placed in a patient predisposed to having recurrent encounters with pulmonary embolism as a preventive measure, have been employed for the last fifteen years. Examples of these types of filters include the Mobid-Uddin umbrella, the Kimray-Greenfield vena cava filter, and the Gunther vena caval filter. The following patient conditions may lead a physician to install an inferior vena caval filter for prophylaxis: a patient having a pulmonary embolism or extensive deep venous thrombosis and absolute contraindication for anticoagulation, a patient suffering from major bleeding on anticoagulation for embolism or venous thrombosis, a patient having a recurrent embolism leading to hemodynamic compromise, a patient with failure of adequate anticoagulation to prevent recurrent thromboembolic disease, a patient with chronic corpulmonale from multiple pulmonary emboli, a patient with a septic embolism, or a patient who has had an embolectomy. In a study of 1133 patients who have been provided with inferior vena cava filters 44% received them due to complications or failure of anticoagulation, 23% received them because of heparin was contraindicated, 13% received them because of caval/iliofemoral vein thrombosis, 8% received them as a prophylactic measure, and 8% received them due to severe pulmonary embolism during initial therapy.

Even though inferior vena caval filters have been in use for over a decade, their popularity is on the decline. These filters are left in the patient for life and lead to venous stasis and form a nidus for recurrent embolization. The Mobid-Uddin filter has been withdrawn because it had an operative mortality rate of 15% and recurrent embolization rate of 45%. The Kimray-Greenfield filter has had more favorable results with an operative mortality rate of 5%, venous problems of 38%, and recurrent embolization of 4%.

No products are currently available which can be used to temporarily prevent a pulmonary embolism in the clinical setting. For example, an obese women who has fallen down a flight of stairs, suffered injuries to her lower extremities, and has laid in bed for several days before reporting to the hospital in a bloated condition is very likely, as discussed above in conjunction with the risk factors and conditions which predispose a patient to a pulmonary embolism, to suffer a pulmonary embolism during routine surgery on her lower body. Other such patients, i.e, car accident victims, etc., are regularly encountered by the physician in the emergency room. What is needed is a device which the physician can use to temporarily protect the patient during the risk period for pulmonary embolism such as during and after surgery, but which can be easily removed when the patient is clear of the danger of a pulmonary embolism.

SUMMARY OF THE INVENTION

It is therefore an object of the present invention to provide a pulmonary artery umbrella catheter which will temporarily be placed in a patient's main pulmonary trunk during surgery that functions to detect, prevent, and treat pulmonary emboli.

According to the invention, a multi-sheathed catheter with an umbrella assembly is placed in the patient's main pulmonary trunk during the risk period for pulmonary embolism. The umbrella assembly includes a meshwork connected at on end to the exterior of the outer sheath of the catheter and connected at its other end to the inside diameter of a tubular balloon which encircles the catheter. In use, the umbrella is opened up so that the tubular balloon contacts the inside wall of the pulmonary trunk and allows blood to pass through the meshwork to the lungs, but catches clots and other emboli in the meshwork so that they do not travel to the lung. Means are provided to control the opening and closing of the umbrella from outside the body and the degree of umbrella opening is regulated so as to limit the amount of pressure the balloon exerts on the pulmonary trunk wall. Sensors and monitoring equipment are provided in the catheter so that the presence or absence of an embolus in the meshwork can be accurately determined. For example, doppler sensor instrumentation is used to sense the gradient of blood flow through the meshwork of the umbrella, chemical sensors are placed in front of the umbrella to analyze blood products caught in the meshwork, and an ultrasound probe is positioned in front of and slidable relative to the umbrella such that two dimensional images of matter caught in the meshwork can be displayed. Means for lysing or removing emboli which have been caught by the umbrella are built into the catheter system. For example, drug dispensing conduits pass through the catheter and are positioned at a point just in front of the umbrella such that drugs such as heparin or lysing agents such as urokinase, streptokinase, or TPA can be sprayed directly on the clot. For larger clots, an ultrasonic means is attached to the catheter at a point in front of the umbrella such that the clots can be mechanically broken apart. Even larger clots are drawn inside the catheter by closing the umbrella and are removed by vacuum suction. The catheter also has the advantage of being useable as a temporary blood bypass conduit if an extremely massive embolus is caught by the umbrella that cannot be lysed or removed.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
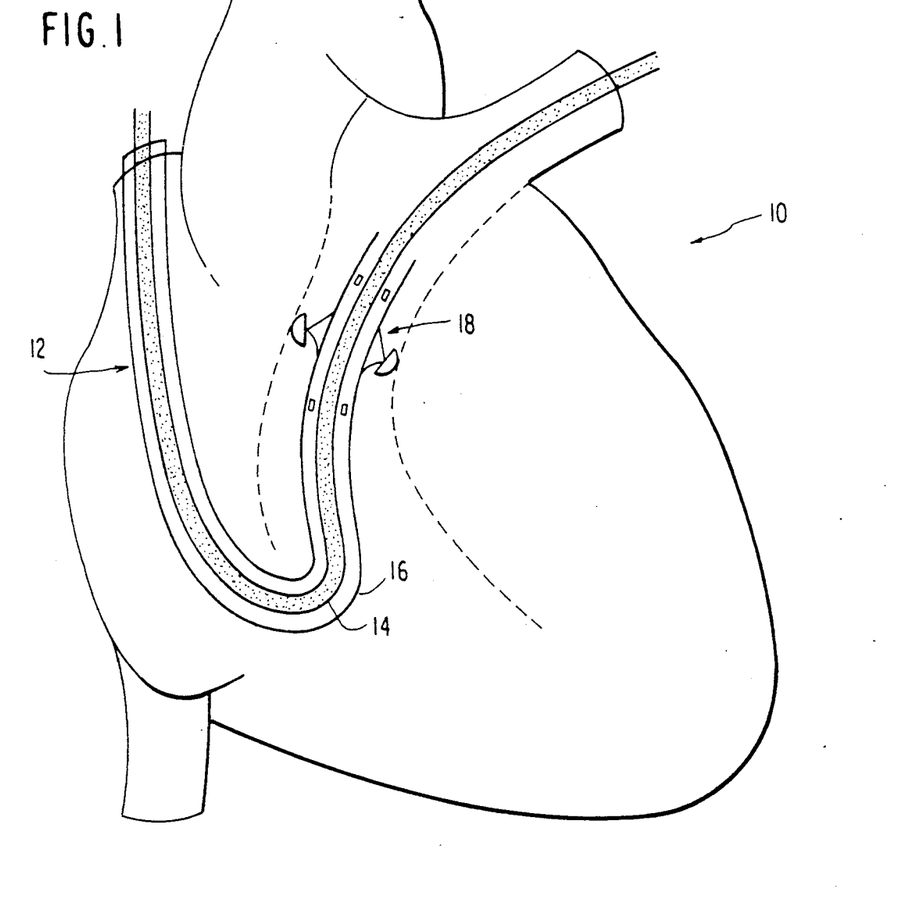
FIG. 1 is a cut-away side view of a human heart having a multisheathed catheter having an umbrella positioned in the pulmonary artery trunk.

Referring now to the drawings, and more particularly to FIG. 1, there is shown a human heart 10 having a multi-sheathed catheter 12 positioned therein. The multisheathed catheter 12 includes an inner guide 14 and an exterior sheath 16 including a circumferentially attached umbrella 18, and can contain several other interior sheathes (not shown). The inner guide 14 can be a balloon floatation catheter of the Swan-Ganz type, another catheter, a wire, or any other suitable means for positioning the exterior sheath 16 so that the umbrella 18 is located in the base of the pulmonary trunk of the heart 10. The catheter 12 can be inserted via either the internal jugular, subclavian or femoral route, as is the standard medical practice for inserting catheters.

Preferably, the internal guide 14 is a Swan-Ganz catheter which is introduced and advanced to the pulmonary artery and a pulmonary capillary wedge is recorded. Then, the external sheath 16 is advanced to a position in the heart 10 using fluoroscopic or echo guidance such that the umbrella 18 can be opened and positioned in the distal segment of the pulmonary trunk. As will be described below, by adjusting the tension on the umbrella 18 and adjusting the air pressure in its outer balloon, the umbrella 18 can be secured safely within the pulmonary trunk. Ideally, the position of the umbrella 18 within the pulmonary trunk can be adjusted forward and backward slightly on a periodic basis to decrease the chance of the pulmonary trunk experiencing trauma due to pressure from the umbrella 18. After the umbrella 18 is positioned properly within the pulmonary trunk, the ultrasonic system, pressure transducers, flow meters, and echo system (not shown but discussed below) are calibrated. After calibration, the system is operational and is used to temporarily halt the progress of emboli into the lungs. Unlike inferior vena caval filters, the present invention is (a) positioned within the pulmonary trunk as opposed to the inferior vena cava, (b) used only temporarily during the risk period and up to 7-10 days thereafter, rather than being a permanent implanted device, and (c) not only halts the thrombi from progressing to the lungs, but also provides various means to remove and destroy the thrombi.

Figure 2:
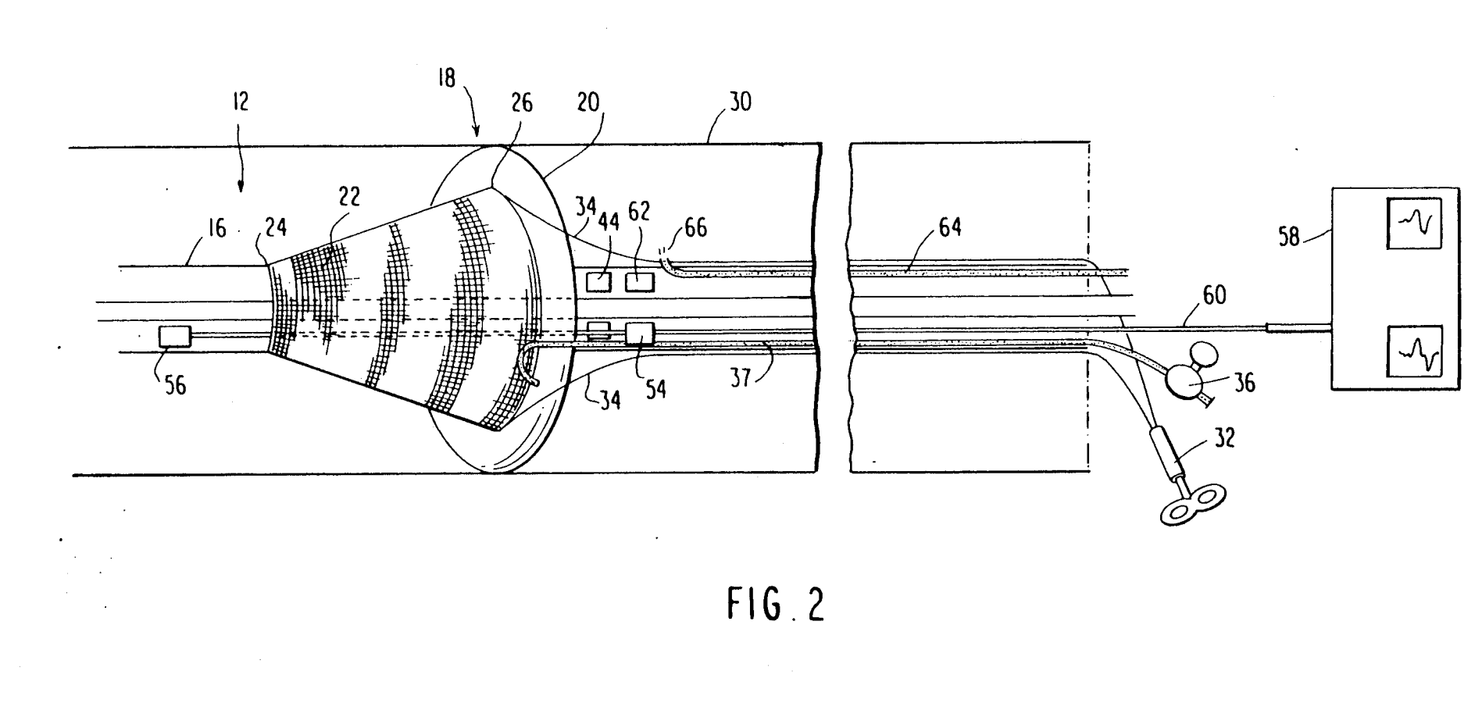
FIG. 2 is a cut-away side view of multisheathed catheter with an umbrella in accordance with the present invention.

FIG. 2 shows the umbrella 18 includes a tubular balloon 20 encircling the catheter 12 and a meshwork 22 connected at one end 24 to the exterior sheath 16 and at its other end 26 to the balloon 20. The meshwork 22 is composed of non-thrombogenic material and is coated with anticoagulants that are slowly released. The meshwork 22 is loose enough to allow free flow of blood and plasma therethrough, but obstructs larger objects, i.e., greater than 3 mm in size.

Figure 3:
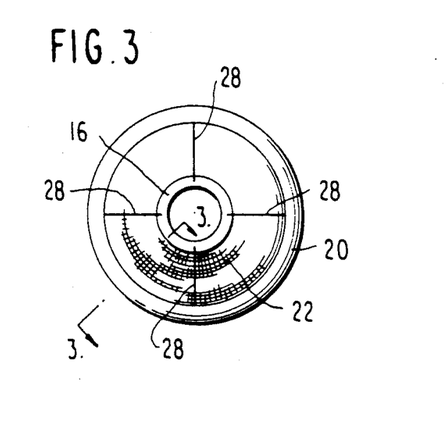
FIG. 3 is an end view of an opened umbrella on a multisheathed catheter.

FIG. 3 shows metallic struts 28 affixed to the exterior sheath 16, which pass through the meshwork 22, and are biased outwardly. The metallic struts 28 can be affixed to the exterior sheath 16 by having there ends embedded therein or by any other suitable means. The metallic struts 28 serve the function of making the umbrella 18 naturally biased to its open position.

Returning to FIG. 2, the balloon 20 portion of the umbrella 18 is biased against the inside wall 30 of the pulmonary trunk; however, the degree of force exerted against the wall 30 is carefully regulated so as to reduce trauma. The degree of umbrella 18 opening is primarily controlled by the tension control syringe 32. The tension control syringe 32 is connected to the balloon 20 by cords 34 which can run within loops (not shown) or a sheath (not shown) positioned outside the external sheath 16, or they may run within the external sheath 16 and pass through peripheral openings about the circumference of the external sheath 16. Preferably, more than one cord 34 is provided so that the umbrella 18 can be evenly pulled toward the external sheath 16 using the tension control syringe 32. By manipulating the tension control syringe 32, the physician can adjust the degree of opening of the umbrella 18 so that the balloon 20 barely touches the wall 30 of the pulmonary trunk, thereby reducing the pressure on the wall 30, yet fully encircles and hugs the wall 30. Because the degree of opening of the umbrella 18 is controllable in this manner, the catheter 12 is readily adaptable to different sized pulmonary trunks. The degree of umbrella 18 opening is also secondarily controlled by regulating the amount of inflation of the balloon 20. A pressure syringe 36 is connected to the balloon 20 by line 37 and includes a transducer (not shown) which senses the pressure inside the balloon 20. The sensed pressure signal can be sent to a display (not shown) for monitoring by the physician. Ideally, the pressure in the balloon 20 should be just enough to maintain it in an expanded state and provide a cushioning affect against the wall 30. Hence, if there is any movement of the umbrella 18 caused by blood flow, the transmitted force from the blood flow is minimized.

Figure 4:
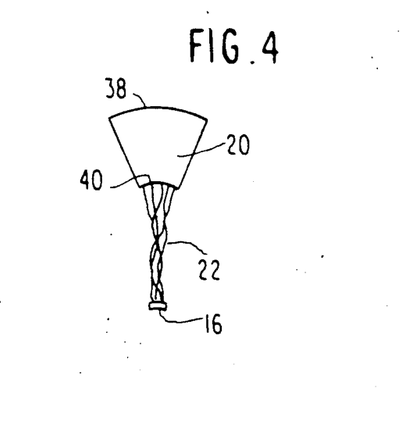
FIG. 4 is a cross-sectional side view of the multisheathed catheter shown in FIG. 3 taken along line 3—3.

FIG. 4 shows that the outer wall 38 of the balloon 20 is preferably larger than the inner wall 40 which is connected to the meshwork 22 of the umbrella 18. Increasing the surface contact area of the balloon 20 as shown in FIG. 4 should reduce the pressure exerted on any one part of the contacted pulmonary artery endothelium 30. The balloon 20 primarily serves the function of acting as a cushion for the pulmonary artery endothelium 30 and is preferably made of a soft expansible material so as to minimize trauma.

Figure 5:
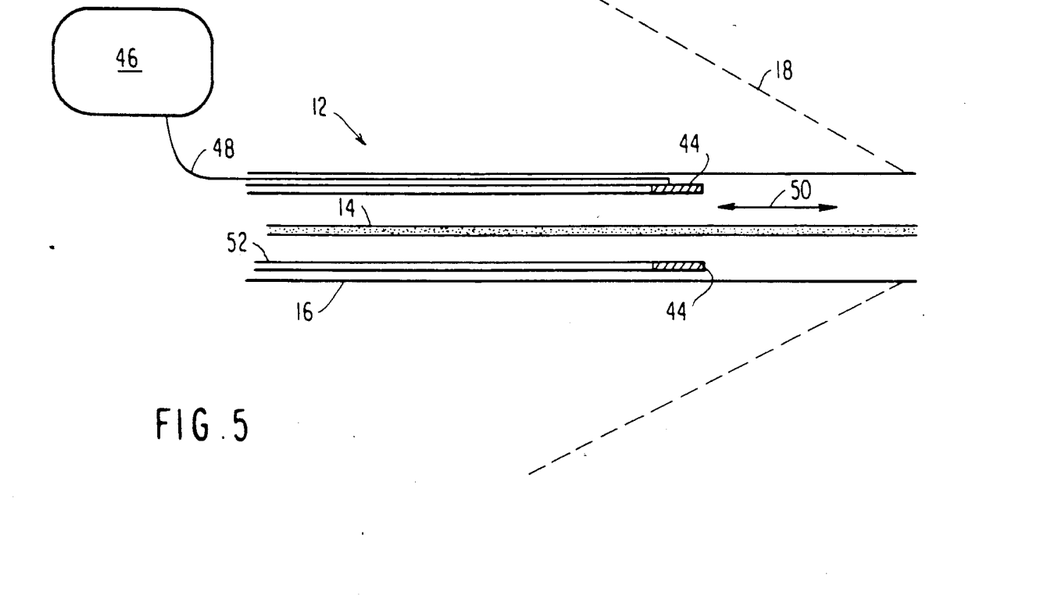
FIG. 5 is a cross-sectional side view of a multisheathed catheter with an umbrella in accordance with the present invention which specifically shows the positioning of a two dimensional ultrasound echo probe.

Referring to FIGS. 2 and 5, a two dimensional ultrasound echo probe 44 is placed in a circumferential fashion in front of the umbrella 18. Several suitable echo probes are currently commercially available and have been used in medicine to visualize intravascular structures. The echo probe 44 presents a two-dimensional image on display 46, via connection line 48, so that the physician can evaluate the inner surface of the umbrella 18. Preferably, the echo probe 44 can be slid back and forth, as indicated by double ended arrow 50, such as by mounting the echo probe 44 on the end of an interior catheter 52, on the end of a catheter (not shown) external to the exterior sheath 16, setting up the echo probe 44 to slide within a guide (not shown) in the exterior sheath 16, or by some other suitable means, so that the physician can visually see a two dimensional cross-sectional depiction of the umbrella 18 along its entire length.

In addition to two dimensional imaging provided by echo probe 44, the multisheathed catheter is also equipped with doppler, impedance, flow or pressure transducers 54 and 56, or combinations thereof. If pressure transducers 54 and 56 are used, they can be either electronic or fluid filled. The doppler, impedance, flow, or pressure transducers 54 and 56 are positioned on opposite sides of the umbrella 18 so that the transducer 54 makes measurements on the heart 10 side and transducer 56 makes measurements on the lungs side of the umbrella 18. The transducers 54 and 56 measure blood flow, velocity, resistance and pressure signals from their respective positions and the measurements are transmitted to display 58 via line 60. If an embolus is trapped in the umbrella 18 and occludes a part of the inner surface of the meshwork 22, a differential will develop across the umbrella 18 which can be detected as (1) a pressure difference, (2) a change in flow velocity, and (3) an impedance between transducer 54 and transducer 56. This differential can be computed, analyzed, and reflected externally on display 58 which will alert the physician that there is entrapment of an object in the umbrella 18.

Chemical sensors 62, positioned on or in the exterior sheath 16 just in front of the umbrella 18, can also be provided for detecting blood products produced by an embolus. The chemical sensors 62 would also be connected to an external alarm system like transducers 54 and 56 and it is noted that the connection to the chemical sensors 62 and transducers 54 and 56 can be either via radio link or straight line connection as shown at 60.

Once a clot or emboli is caught in umbrella 18 and the physician is alerted of its presence by visualizing it with the two dimensional echo probe 44 and detecting it with transducers 54 and 56 and sensors 62, the catheter 12 is equipped with a number of means by which the physician can handle the problem. If there is no contraindication to thrombolysis, thrombolytic agents that are selective, such as TPA, can be administered directly to the clot via fluid channel 64 which, as shown in FIG. 2, sprays the agent 66 from the catheter 12 from a point just in front of the umbrella 18. Because of the proximity to the embolus, it is likely that the dose required to lyse the clot is probably going to be much smaller than doses which are routinely administered in hospitals today to treat pulmonary emboli (i.e., none of today's methods spray agents 66 directly on a trapped clot). Moreover, if clot lysis is achieved using the sprayed agent 66, further anticoagulation may not be required.

Figure 6:
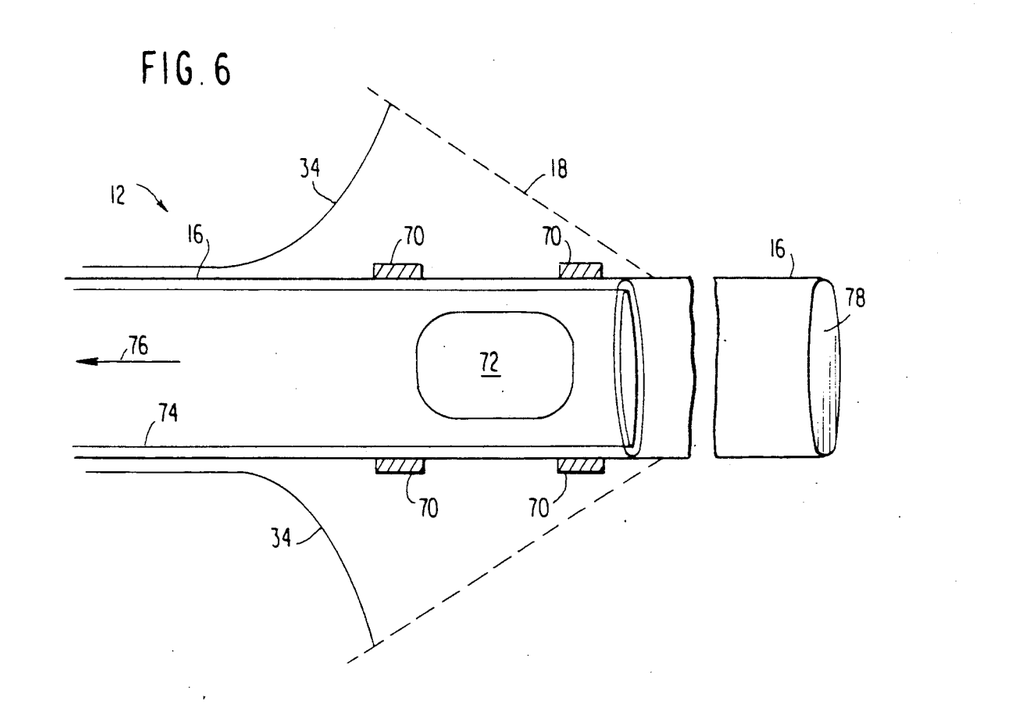
FIG. 6 is a cross-sectional side view of a multisheathed catheter with an umbrella in accordance with the present invention which specifically shows ultrasonic probes for breaking apart blood clots and openings in the external sheath which, when the interior catheter is retracted, allow blood clots to be removed via suction.

FIG. 6 shows portions of the multisheathed catheter 12 of FIG. 2 underneath the umbrella 18. If a clot caught in the umbrella has become organized and hard, or it constitutes tissue material or other foreign matter not likely to be lysed by thrombolytic therapy with the agents 66 described in conjunction with FIG. 2, or if anticoagulation and thrombolytic therapy is contraindicated, clot destruction can be performed by high velocity ultrasound energy. Ultrasound energy has been shown to be effective for clot lysis in vitro. Ultrasound probes 70 can be arranged longitudinally or circumferentially on the outer surface of exterior sheath 16. The probes 70 can be energized either directly by line connection (not shown) or by radio transmission. Referring to both FIGS. 2 and 6, preferably, after an embolism is caught in the umbrella 18 and detected using the two dimensional echo probe 44, the transducers 54 and 56, and the chemical sensors 62, the physician closes the umbrella 18 down on the clot using the tension control syringe 32 to pull down on cords 34. Closing the umbrella 18 brings the clot within close proximity of the probes 70 and also re-establishes the free flow of blood to the lungs. For fresh clots, the ultrasound energy and duration of vibration will be minimal. A typical example of a suitable probe 70 the Ultrasonic Flexible Solid Wire Titanium Probe which is connected to an Ultrasonic Lithotripsy Generator (model PDX-1) available from Blackstone Ultrasonics of New York. After the clot is destroyed by ultrasound energy, its remains can be treated with lysing agents 66 as described in conjunction with FIG. 2 and the umbrella 18 can be opened back up to the operational configuration shown in FIG. 2.

Figure 8:
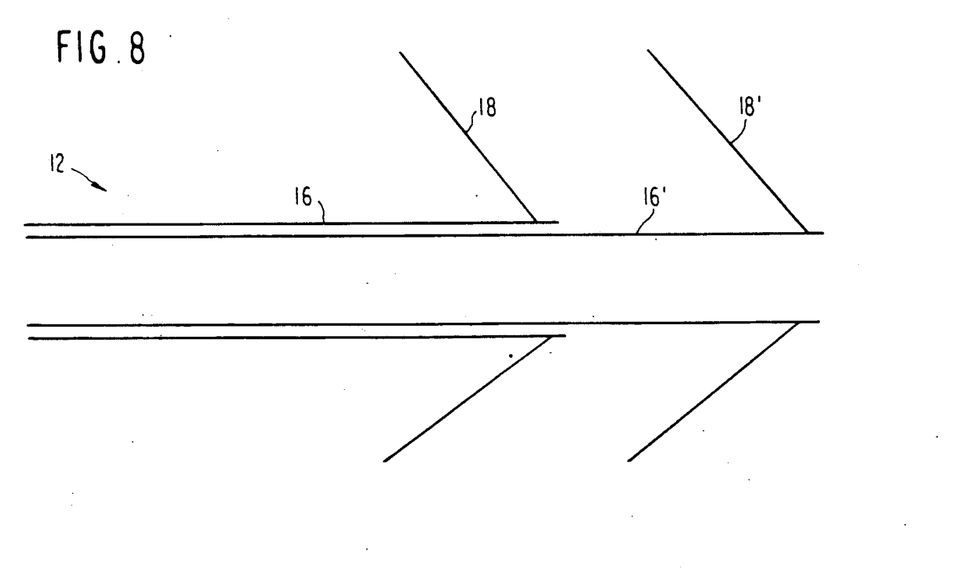
FIG. 8 is a schematic side view of a multisheathed catheter with two serially positioned umbrella members.

It is anticipated that the multisheathed catheter 12 can be provided with a second, back up umbrella 18' on another sheath 16' as shown in FIG. 8, which provides protection from emboli when the primary umbrella 18 is closed for ultrasonic treatment of a trapped clot. If the catheter 12 is so equipped, it is anticipated that control of the second, back up umbrella, which will be positioned closer to the lungs, will be accomplished in the same manner described above for the primary umbrella 18.

Returning to FIG. 6, the exterior sheath 16 may have one or more peripheral openings 72 which allow clots that cannot be destroyed with lysing agents 66 or by ultrasound energy from probes 70 to be drawn into the lumen and removed by vacuum suction. In the configuration shown in FIG. 6, an inner catheter 74 snugly fits inside the exterior sheath 16. When the inner catheter 74 is withdrawn in the direction of arrow 76, clots are free to enter the lumen via peripheral openings 72. The umbrella 18 can be used to push the clot into the opening 72 by pulling back on cords 34. Once the clot is in the lumen, suction pressure can be applied to the lumen of the catheter and exerted in the direction of arrow 76 by well known techniques. A cap 78 can be fitted on the end of exterior sheath 16 by well known techniques so that suction pressure works properly. Preferably, the catheters used in the multisheathed catheter 12 are sized so that larger emboli can be accommodated, i.e., an 8-11 french catheter. If suction is successful for removing the clot out of the patient's body, the lumen of the catheter 12 is closed by moving the inner catheter 74 towards the position shown in FIG. 6 so that the peripheral opening 72 in the exterior sheath 16 is closed off and the umbrella 18 is re-opened. Hence, the catheter 12 can be left in position to guard against further emboli.

Figure 7:
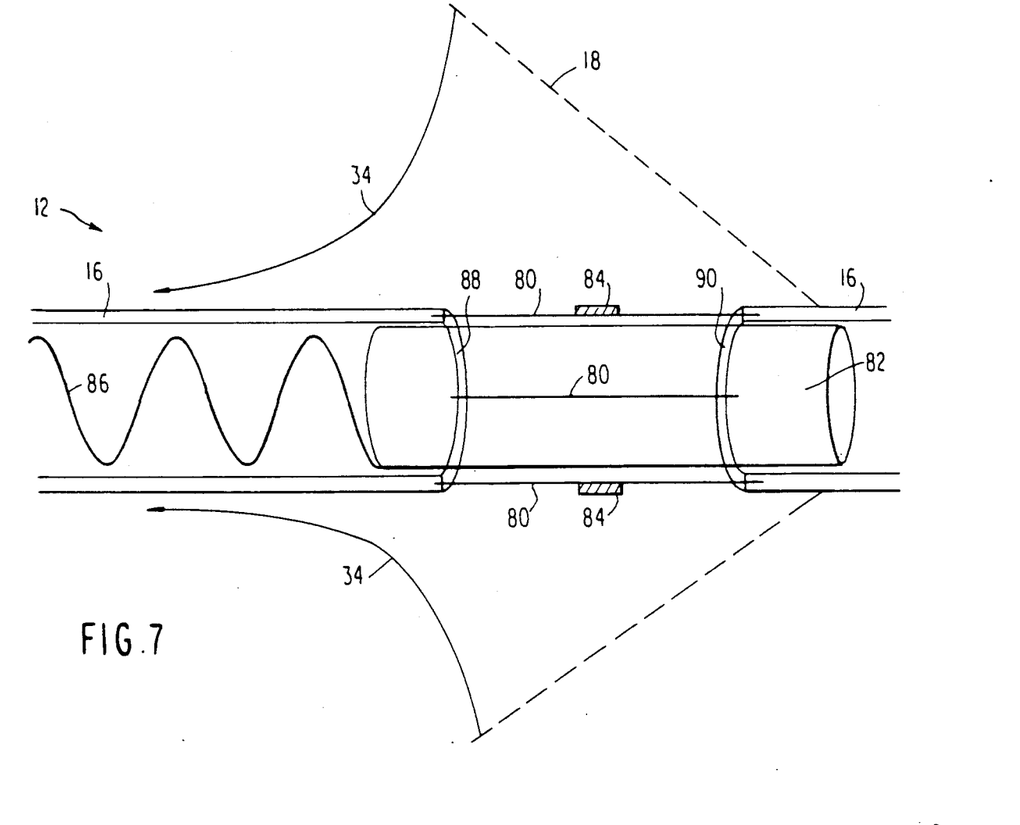
FIG. 7 is a cross-sectional side view of a multisheathed catheter with an umbrella in accordance with the present invention which shows an alternative configuration to that shown in FIG. 6 for removing blood clots via ultrasound and suction.

FIG. 7 shows an alternative configuration to FIG. 6 wherein the exterior sheath 16 is split at a region underneath the umbrella 18. Metallic struts 80, which are preferably embedded in the ends 88 and 90 of the exterior sheath 16 as shown in FIG. 7, hold the two pieces of the exterior sheath 16 firmly together. A telescoping segment 82 blocks the opening in the exterior sheath 16. As described in conjunction with FIG. 6, ultrasonic probes 84 are positioned underneath the umbrella 18 so that hardened clots and other tissue material and foreign material caught in the umbrella 18 can be drawn towards the probes 84 by pulling back on cords 34 and destroyed by ultrasound energy. Preferably, the ultrasound probes 84 can be mounted directly on the metallic struts 80 so that the struts 80 vibrate with the probes 84 and help destroy the clot. Larger clots are drawn into the lumen of the catheter 12 by retracting the telescoping segment 82 using a cork screw mechanism 86 as is standard, after which the clots are removed via suction pressure generated external to the body. After a clot is succesfully removed by suction, the cork screw 86 can be rotated so as to close off the opening in the sheath 16 and the umbrella can be re-opened.

In regard to both FIGS. 6 and 7, if suction pressure is not possible or the clot is so large that it cannot be destroyed by the mechanisms described above, the umbrella 18 can be pulled into the right atrium, the internal jugular, or the subclavian vein, depending on which route was the method of insertion. This is accomplished by closing the umbrella 18 on the clot and retracting the exterior sheath 16 from the position shown in FIG. 1. By this mechanism, a large clot which would invariably have been fatal will have been pulled into a distant vessel and temporarily contained at a point where it can be surgically removed by being captured by the umbrella 18.

The multisheathed catheter 12 is also designed to temporarily handle massive emboli which are too large to be captured and destroyed with the umbrella 18 by the several methods described above. A temporary re-routing of blood flow is accomplished with the catheter 12 by keeping the umbrella 18 in the inflated, open configuration to obstruct the progression of the embolus into the lungs and then, via a vascular pump, connect the femoral vein or artery to the lumen of the catheter 12 on the external end (outside the body). Preferably, the internal catheters are an 8 french or larger catheter so that sufficient blood can be delivered to the lungs per minute to maintain the circulation. While the patient is likely to be in shock from this treatment, the treatment allows the physician extra time in order to plan surgical removal of the clot.

While the invention has been described in terms of its preferred embodiment wherein a multisheathed catheter including an umbrella member comprised of a tubular, inflatable balloon and a meshwork of non-thrombogenic material is placed in the pulmonary trunk of a patient during surgery to halt the progress of emboli to the lungs, those skilled in the art will recognize that the invention can be practiced with modification within the scope of the appended claims.

Having thus described my invention, what I claim as new and desire to secure by Letters Patent is as follows:

1. An intracardiac catheter, including:
   a sheath;
   an umbrella sized to fit within a patient's pulmonary artery connected to said sheath, said umbrella allowing blood and plasma to pass through freely but trapping emboli;
   a means for biasing said umbrella to an open position away from said sheath;
   means for controlling the degree of opening of said umbrella;
   means for detecting the presence of emboli trapped in said umbrella; and
   means for treating emboli trapped in said umbrella.

2. An intracardiac catheter as recited in claim 1 wherein said umbrella is comprised of a mesh material connected at one end to said sheath and connected at another end to a tubular member which encircles said sheath.

3. An intracardiac catheter as recited in claim 2 wherein said tubular member is an inflatable balloon.

4. An intracardiac catheter as recited in claim 3 wherein said balloon has a larger outside surface for contacting the wall of said pulmonary artery and a smaller inside surface connected to said meshwork.

5. An intracardiac catheter as recited in claim 1 wherein said means for biasing said umbrella to an open position includes flexed members positioned within said umbrella that are connected at one end to said sheath and are biased away from said sheath at another end.

6. An intracardiac catheter as recited in claim 1 wherein said means for controlling the degree of opening of said umbrella includes cords connected to said umbrella at points distant from said sheath, said cords being retractable such that a free end of said umbrella is capable of being drawn towards said sheath.

7. An intracardiac catheter as recited in claim 6 wherein said cords can be retracted to a point where said free end of said umbrella is in contact with said sheath.

8. An intracardiac catheter as recited in claim 6 wherein said means for contolling the degree of opening of said umbrella further includes an inflatable balloon positioned at the free end of said umbrella and a means for controlling the pressure inside said inflatable balloon.

9. An intracardiac catheter as recited in claim 1 wherein said means for detecting the presence of larger emboli trapped in said umbrella includes an ultrasound probe which outputs signals to a display, said display capable of showing two dimensional images.

10. An intracardiac catheter as recited in claim 9 wherein said ultrasound probe is slidable towards and away from said umbrella.

11. An intracardiac catheter as recited in claim 1 wherein said means for detecting the presence of larger emboli trapped in said umbrella includes means for detecting a differential across said umbrella.

12. An intracardiac catheter as recited in claim 11 wherein said means for detecting a differential comprises first and second pressure gauges positioned on opposite sides of said umbrella.

13. An intracardiac catheter as recited in claim 11 wherein said means for detecting a differential comprises first and second doppler transducers positioned on opposite sides of said umbrella.

14. An intracardiac catheter as recited in claim 11 wherein said means for detecting a differential comprises first and second impedance transducers positioned on opposite sides of said umbrella.

15. An intracardiac catheter as recited in claim 11 wherein said means for detecting a differential comprises first and second flow transducers positioned on opposite sides of said umbrella.

16. An intracardiac catheter as recited in claim 1 wherein said means for detecting the presence of emboli trapped in said umbrella includes a chemical sensor positioned in front of said umbrella.

17. An intracardiac catheter as recited in claim 1 wherein said means for detecting the presence of emboli trapped in said umbrella includes an ultrasound probe which outputs signals to a display, said display capable of showing two dimensional images, and a means for sensing a differential across said umbrella.

18. An intracardiac catheter as recited in claim 1 wherein said means for treating emboli trapped in said umbrella includes a means for transporting lysing agents to said emboli trapped in said umbrella.

19. An intracardiac catheter as recited in claim 1 wherein said means for treating emboli trapped in said umbrella includes an ultrasound probe positioned adjacent said umbrella for applying ultrasound energy to said emboli.

20. An intracardiac catheter as recited in claim 1 wherein said means for treating emboli trapped in said umbrella includes a means for moving said emboli inside said sheath and a means for applying vacuum suction to said emboli from inside said sheath.

21. An intracardiac catheter as recited in claim 1 wherein said means for treating emboli trapped in said umbrella includes a means for retracting said sheath from said patient's pulmonary artery.

22. A method for protecting a patient from a pulmonary embolism during surgery, comprising the steps of:
   placing a catheter having an attached umbrella inside said patient's pulmonary artery, said umbrella allowing blood and plasma to pass through freely but trapping emboli;
   opening said umbrella inside said patient's pulmonary artery;
   detecting the presence of emboli trapped in said umbrella; and
   treating said emboli trapped in said umbrella.

23. A method as recited in claim 22 wherein said step of placing is performed by fluoroscopic guidance.

24. A method as recited in claim 22 wherein said step of placing is performed by echo guidance.

25. A method as recited in claim 22 wherein said step of opening said umbrella is performed by providing outward biasing members in said umbrella.

26. A method as recited in claim 22 wherein said step of detecting is performed by ultrasound imaging.

27. A method as recited in claim 22 wherein said step of detecting is performed by monitoring a differential across said umbrella.

28. A method as recited in claim 22 wherein said step of detecting is performed by chemically sensing the presence of emboli in said umbrella.

29. A method as recited in claim 22 wherein said step of treating is performed by transporting lysing agents directly to said emboli trapped in said umbrella.

30. A method as recited in claim 22 wherein said step of treating is performed by using ultrasound energy to break apart said emboli trapped in said umbrella.

31. A method as recited in claim 22 wherein said step of treating is performed by drawing said emboli into said catheter and subjecting said emboli to vacuum suction.

32. A method as recited in claim 22 wherein said step of treating is performed by closing said umbrella on said trapped emboli and withdrawing said emboli from said pulmonary artery.

33. An intracardiac catheter, including:
   first and second sheaths;
   first and second umbrellas sized to fit within a patient's pulmonary artery each of which are connected respectively to said first and second sheaths, said first and second umbrellas allowing blood to pass through freely but trapping emboli;
   a means for biasing said first and second umbrellas to an open position away from said sheath;
   a means for controlling the degree of opening of said umbrella;
   a means for detecting the presence of emboli trapped in said first umbrella; and
   a means for treating emboli trapped in said first umbrella.

* * * * *